United States Patent [19]

Yong et al.

[11] Patent Number: 4,874,544
[45] Date of Patent: Oct. 17, 1989

[54] FERROELECTRIC LIQUID CRYSTALS

[75] Inventors: Bak G. Yong; Petra Barth; Demus Dietrich; Detlev Joachimi, all of Halle; Barbara Kampa, Halle-Neustadt; Saskia Köhler, Halle-Neustadt; Kristine Mohr, Halle-Neustadt; Reinhard Paschke, Halle-Neustadt; Gerhard Pelzl, Halle-Neustadt; Ulrich Rosenfeld, Halle; Wolfgang Schäfer, Potsdam; Klaus-Dieter Scherf, Halle; Carsten Tschirske, Halle; Wolfgang Weissflog, Halle-Neustadt; Horst Zaschke, Halle, all of German Democratic Rep.

[73] Assignee: VEB Werk fuer Fernsehelektronik im VEB Kombinat Mikroelektronik, Berlin, German Democratic Rep.

[21] Appl. No.: 151,731

[22] Filed: Feb. 3, 1988

[30] Foreign Application Priority Data

Feb. 19, 1987 [DD] German Democratic Rep. ... 300041

[51] Int. Cl.$^4$ .................... G02F 19/34; C07D 239/02; C07D 285/12
[52] U.S. Cl. .................... 252/299.61; 252/299.5; 252/299.01; 350/350 R; 350/350 S; 544/335; 548/136
[58] Field of Search .......... 252/299.61, 299.5, 299.01; 350/350 S, 350 R; 544/179, 194, 216, 219, 180, 238, 239, 224, 295, 296, 299, 316, 315, 318, 322, 330, 331, 332, 333, 335, 242, 360, 365, 371, 367, 382, 383, 385, 388, 387, 389, 386, 392, 396, 399, 403; 546/277, 255, 296, 290, 301, 300, 298, 299, 304, 314, 326, 330, 329, 334, 335, 339, 340, 341, 342, 346, 348; 549/20–22, 369, 371–375; 548/136; 428/1

[56] References Cited

U.S. PATENT DOCUMENTS

| | | | |
|---|---|---|---|
| 4,592,858 | 6/1986 | Higuchi et al. | 252/299.66 |
| 4,657,695 | 4/1987 | Saito et al. | 252/299.61 |
| 4,725,686 | 2/1988 | Taguchi et al. | 252/299.61 |
| 4,728,458 | 3/1988 | Higuchi et al. | 252/299.65 |
| 4,765,924 | 8/1988 | Inoue et al. | 252/299.61 |

FOREIGN PATENT DOCUMENTS

| | | | |
|---|---|---|---|
| 225195 | 6/1987 | European Pat. Off. | 252/299.61 |
| 248335 | 12/1987 | European Pat. Off. | 252/299.61 |
| 3515373 | 11/1986 | Fed. Rep. of Germany | 252/299.61 |
| 240385 | 10/1986 | German Democratic Rep. | 252/299.01 |
| 240386 | 10/1986 | German Democratic Rep. | 252/299.01 |
| 60-255779 | 12/1985 | Japan | 252/299.61 |
| 61-215374 | 9/1986 | Japan | 252/299.61 |
| 8705018 | 8/1987 | World Int. Prop. O. | 252/299.61 |

Primary Examiner—Teddy S. Gron
Attorney, Agent, or Firm—Jordan and Hamburg

[57] ABSTRACT

Fast-switching displays with memory properties are provided, which can display digits, symbols, and images, and which contain as chemically and thermally stable ferroelectric liquid crystalline substances, according to the invention, liquid crystalline derivatives which contain a chiral alkyl halide residue corresponding to the general formula

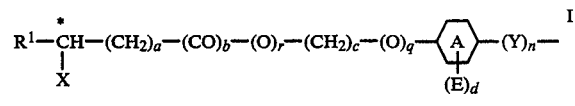

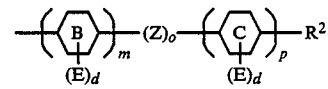

are used in mixtures of one another as well as in conjunction with other liquid crystalline or non-crystalline liquid substances.

18 Claims, No Drawings

FERROELECTRIC LIQUID CRYSTALS

BACKGROUND OF THE INVENTION

This invention concerns ferroelectric liquid crystals useful for fabrication fast-switching displays with memory properties for the display of digits, symbols, and images.

It is known that ferroelectric liquid crystals can be used to fabricate fast-switching displays with memory properties as disclosed by N. A. Clark, S. T. Lagerwall, Appl. Phys. Lett. 36, 899 (1980).

The number of ferroelectric liquid crystal compounds has expanded greatly in recent times, but as yet there are no pure materials with optimal properties (S. T. Lagerwall, J. Wahl, N. A. Clark, Proceed. SIO Symposium, October 1985, San Diego, USA; J. W. Goodby, Science 231, 350 (1986), F. Dahl, S. T. Lagerwall, Ferroelectrics 58, 215 (1984), D. Demus, H. Zaschke, Flussige Kristalle in Tabellen II (Liquid Crystals in Tables II) Leipzig 1984).

Many ferroelectric liquid crystals are not very stable chemically and thermally, have high melting points, or else their spontaneous polarization is insufficient. Because their dipole moments are too small, and consequently the associated spontaneous polarization is also small, the derivatives of the 2-methyl-butyl group and other chiral branched alkyl chains are unfavorable for practical utilization due to their excessively long switching times.

Other ferroelectric liquid crystals contain the azomethine grouping and, as Schiff bases, are not very stable with respect to heat, moisture, and acids.

Some ferroelectric liquid crystals derived from chiral α-chlorocarboxylic acids exhibit excessively high melting points (J. W. Goodby et al., Proceed. of 1983 A. C. S. Meeting, Las Vegas, Nev., 1982; Liquid Crystals and Ordered Fluids, Vol 4, F 1).

SUMMARY OF THE INVENTION

The objective of the invention is to provide fast-switching displays with memory properties, which contain chemically and thermally stable ferroelectric liquid crystal substances.

Another object of the invention is to provide ferroelectric liquid crystals which can be used in fast-switching displays with memory properties.

According to the invention, it has been found that compounds which contain a chiral alkyl halide residue, corresponding to the general formula I $$R^1-\overset{*}{C}H-(CH_2)_a-(CO)_b-(O)_r-(CH_2)_c-(O)_q-\underset{(E)_d}{A}-(Y)_n-$$
$$\underset{(E)_d}{B}_m-(Z)_o-\underset{(E)_d}{C}_p-R^2 \quad I$$

where
a=0, 1 or 2
b, c, d, n, m, o, p, q, r=0 or 1
X=F, Br or Cl
Y=—COO—, —OOC—, —CH$_2$—CH$_2$—, —CH$_2$—O— or —O—CH$_2$—
Z=Y, —CH$_2$—, —N=N— or —N=N(O)—

E=Halogen, —CN, —CH$_3$, —NO$_2$ or —OCH$_3$

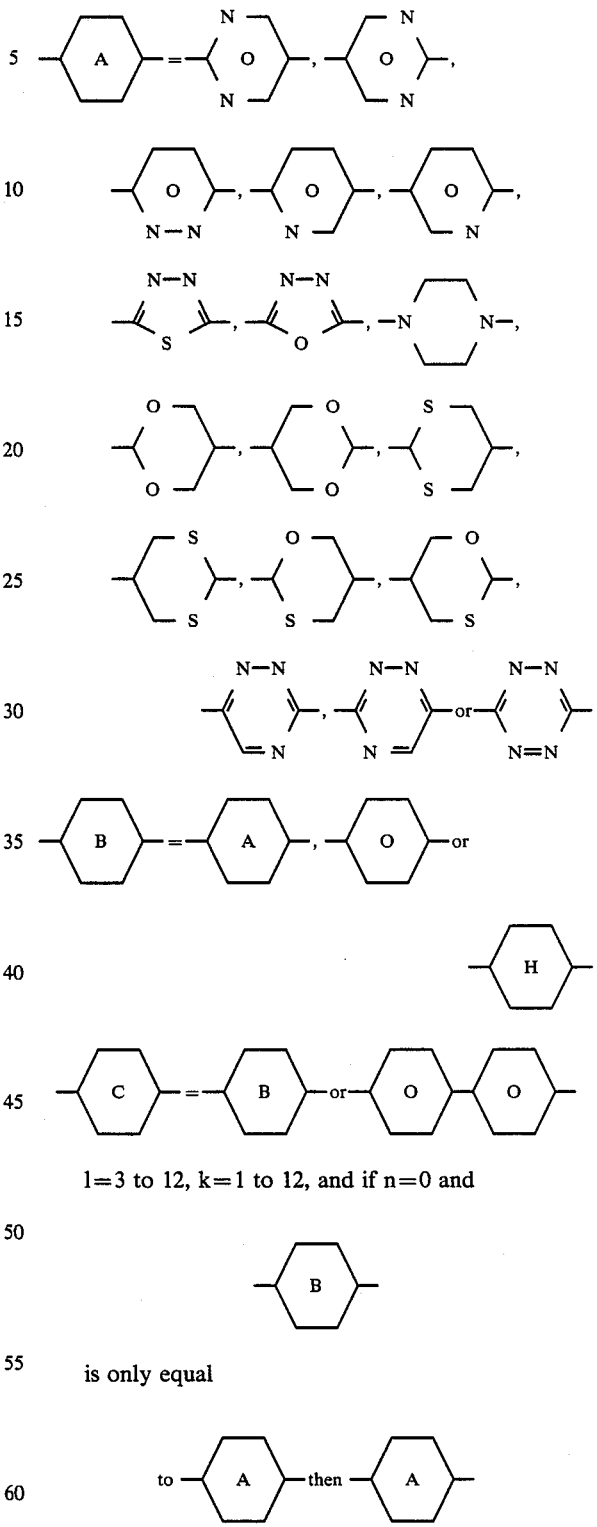

l=3 to 12, k=1 to 12, and if n=0 and

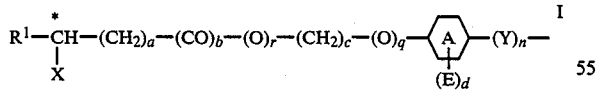

is only equal

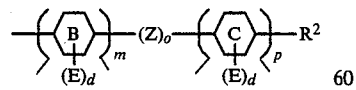

can also be a benzene ring; and if b equals 0, a must equal 1, are ferroelectric liquid crystals.

In mixtures with one another, as well as with other liquid crystal or noncrystalline liquid substances, they form ferroelectric liquid crystal phases and are suitable for use in displays.

The substances are fabricated according to well-known methods, e.g. by esterification of chiral α-halo-carboxylic acids or their derivatives with appropriate hydroxy compounds, according to the diagram:

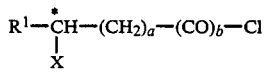

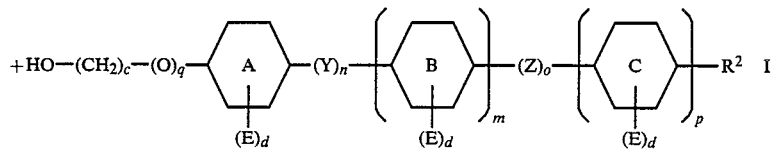

The chiral α-halo-carboxylic acids are obtained by the conversion of commercially obtainable chiral α-amino acids, by splitting the racemates of the α-halo-carboxylic acids or by racemate resynthesis. Other derivatives are produced by esterification with b-halo-carboxylic acids or by reaction with other chiral alkyl halide derivatives.

Due to the high dipole moments of the alkyl halide derivatives, these substances have a high spontaneous polarization and thus have a short switching time in electro-optic displays.

The following examples further illustrate the invention.

EXAMPLES

Example 1

Tables 1 and 4 list the substances relevant to the invention.

Tables 2 and 3 contain already known substances, which are used as components of mixtures.

Here the symbols have the following meaning

K = solid crystalline state
$S^*_C$ = ferroelectric smectic C-phase
$S_A, S_B$ = smectic A-, B-phase
CH = cholesterinic phase
I = isotropic liquid phase
N = nematic phase
$S_X$ = unclassified smectic phase The numbers between the phase designations indicate transition temperatures in degrees C.

TABLE 1

| No. | Structure | K | | $S_x$ | | $S_C^*$ | | $S_A$ | | CH | | I |
|---|---|---|---|---|---|---|---|---|---|---|---|---|
| No. 1 | (CH₃)₂CH—*CHCOO—⟨phenyl⟩—C(=N)—CH=N—⟨phenyl⟩—OC₆H₁₃ (with Cl) | • | 108 | • | 137 | • | 158 | • | 196 | — | — | • |
| No. 2 | C₂H₅—*CH(CH₃)—CHCOO—⟨phenyl⟩—pyrimidine—⟨phenyl⟩—OC₆H₁₃ (with Cl) | • | 140 | — | — | | | • | 190 | — | — | • |
| No. 3 | (CH₃)₂CH—*CH(Cl)—CH—COO—⟨phenyl⟩—pyrimidine—⟨phenyl⟩—C₁₀H₂₁ | • | 110 | (• | 95) | • | 145 | • | 172 | — | — | • |
| No. 4 | (CH₃)₂CH—*CH(Cl)—CH—COO—⟨phenyl⟩—pyrazine—⟨phenyl⟩—OC₅H₁₁ | • | 148 | — | — | • | 179 | • | 186.5 | — | — | • |
| No. 5 | (CH₃)₂CH—*CH(Cl)—CH₂—COO—⟨phenyl⟩—pyrazine—⟨phenyl⟩—OC₅H₁₁ | • | 132 | — | — | • | 159 | • | 168 | — | — | • |
| No. 6 | C₂H₅—*CH(CH₃)—CH(Cl)—COO—⟨phenyl⟩—pyridazine—⟨phenyl⟩—OC₅H₁₁ | • | 153 | — | — | — | — | • | 172 | • | 185 | • |
| No. 7 | (CH₃)₂CH—*CH(Cl)—CH—COO—⟨phenyl⟩—thiadiazole—⟨phenyl⟩—OC₉H₁₉ | • | 105 | — | — | • | 158 | — | — | • | 162 | • |
| No. 8 | CH₃—*CHCl—CH₂—COO—⟨phenyl⟩—C(=N)—CH=N—⟨phenyl⟩—C₁₀H₂₁ | • | 137 | — | — | • | 138 | — | — | 238(Z) | — | — | • |

TABLE 1-continued

| No. | Structure | K | $S_x$ | | $S_c^*$ | $S_A$ | CH | I |
|---|---|---|---|---|---|---|---|---|
| No. 9a | CH₃—*CHCl—CH₂COO—〈phenyl〉—〈pyridine-C₇H₅〉 | • 75 | — | — | — | — | — | • |
| No. 9b | CH₃—*CHCl—CH₂COO—〈phenyl〉—〈pyridine〉—〈phenyl-OC₆H₁₃〉 | • 150 | (• 133) | — | — | — | — | • |
| No. 9c | CH₃—*CHCl—CH₂COO—〈phenyl〉—COO—〈phenyl-OC₆H₁₃〉 | • 63 | — | — | — | — | — | • |
| No. 9d | CH₃—*CHCl—CH₂COO—〈phenyl〉—OOC—〈phenyl-C₁₀H₂₁〉 | • 55 | • 58 | • 66[1] | — | • 87 | • |
| No. 9e | CH₃—*CHCl—CH₂COO—〈phenyl〉—〈phenyl-OC₁₀H₂₁〉 | • 96 | (• 95) | • 108[1] | — | • 93 | • |
| No. 9f | CH₃—*CHCl—CH₂COO—〈phenyl〉—OOC—〈phenyl〉—〈phenyl-OC₈H₁₇〉 | • 106 | • 136 | • 154[1] | — | • 220 | • |

[1] Unclassified smectic phase

TABLE 2

| | | K | $S_C^*$ | $S_A$ | CH | I |
|---|---|---|---|---|---|---|
| No. 9g | $(CH_3)_2CH-\overset{*}{C}H(Cl)-COO-\phi-COO-\phi-[pyrimidine]-C_9H_{19}$ | • 73 | (• 69) | — | — | • 157 | • |
| No. 9h | $(CH_3)_2CH-\overset{*}{C}H(Cl)-COO-\phi-\phi-OOC-\phi-OC_9H_{17}$ | • 87 | • 154 | — | — | • 188 | • |
| No. 10 | $(CH_3)_2CH-\overset{*}{C}H(Cl)-COO-\phi-\phi-OOC-\phi-OC_6H_{13}$ | • 86 | • 132 | — | — | • 196 | • |
| No. 11 | $(CH_3)_2CH-\overset{*}{C}H(Cl)-COO-\phi-OOC-\phi-OC_8H_{17}$ | • 49 | • 58 | — | — | • 72 BP74 | • |
| No. 12 | $(CH_3)_2CH-\overset{*}{C}H(Cl)-COO-\phi-OOC-\phi-OC_{10}H_{21}$ | • 66 | (• 45) | • 68 | • 70 BP72 | • |
| No. 13 | $(CH_3)_2CH-\overset{*}{C}H(Cl)-COO-\phi-OOC-\phi-OC_{12}H_{25}$ | • 62 | (• 42) | • 69 | — | — | • |

TABLE 3

| | | K | $S_C$ | $S_A$ | N | T |
|---|---|---|---|---|---|---|
| No. 14 | $C_8H_{17}OCOO-\phi-COO-\phi-C_9H_{19}$ | • 34 | • 34 | — | — | • 56 | |
| No. 15 | $C_8H_{17}O-\phi-COO-\phi-OC_6H_{13}$ | • 55 | • 66 | — | — | • 89.5 | • |
| No. 16 | $C_8H_{17}O-\phi-[pyrimidine]-C_9H_{19}$ | • 33 | • 56.5 | • 74.5 | — | — | • |
| No. 17 | $C_6H_{13}-O-\phi-[pyrimidine]-C_9H_{19}$ | • 24 | • 43 | • 69.5 | • 70.5 | | • |

TABLE 4

| | | K | I |
|---|---|---|---|
| No. 18 | $C_8H_{17}O-\phi(Cl)-COO-\phi-OOC-\overset{*}{C}H(Cl)-CH(CH_3)_2$ | • 80 | • |

TABLE 4-continued

| No. | Structure | K | S_c | S_A | CH | I |
|---|---|---|---|---|---|---|
| 19 | $C_{10}H_{21}O$—(Ph, 3-Cl)—COO—(Ph)—OOC—*CH(Cl)—CH(CH_3)_2 | | ● | | 73 | ● |
| 20 | $C_8H_{17}O$—(Ph)—COO—(Ph)—CH_2—OOC—*CH(Cl)—CH(CH_3)_2 | | ○ | | 41 | ● |
| 21 | $C_{10}H_{21}O$—(Ph)—COO—(Ph)—CH_2—OOC—*CH(Cl)—CH(CH_3)_2 | | ● | | 37 | ● |

| No. | Structure | K | S_c | S_A | CH | I |
|---|---|---|---|---|---|---|
| 22 | $C_8H_{17}O$—(Ph)—COO—(Ph)—COO—(Ph)—CH_2OOC—*CH(Cl)—CH(CH_3)_2 | ● 72 | (● 54) | ● 118 | ● 124–5 | ● |
| 23 | $C_5H_{11}$—N(C=O)(C=S–S)=CH—(Ph)—OOC—*CH(Cl)—CH(CH_3)_2 | ● 108 | — | — | — | ● |
| 24 | $C_6H_{13}$—(pyrimidine)—(Ph)—OCH_2—CH_2—OOC—*CH(Cl)—CH(CH_3)_2 | ● 44 | — | — | — | ● |
| 25 | (benzotriazole N-oxide)—OOC—(Ph)—OOC—*CH(Cl)—CH(CH_3)_2 | ● 142 | — | — | ● 165 | ● |

| No. | Structure | K | S_c | N | is |
|---|---|---|---|---|---|
| 26 | $(CH_3)_2CH$—*CH(Cl)—C(=O)—O—(Ph)—C(=N–N)–S—(Ph)—$OC_5H_{11}$ | ● 157.5 | ● (157) | ● 170 | ● |
| 27 | $(CH_3)_2CH$—*CH(Cl)—C(=O)—O—(Ph)—C(=N–N)–S—(Ph)—$OC_8H_{17}$ | ● 80 | ● 167.5 | ● 177 | ● |
| 28 | $(CH_3)_2CH$—*CH(Cl)—C(=O)—O—(Ph)—C(=N–N)–S—(Ph)—$OC_9H_{19}$ | ● 108 | ● 165.5 | ● 168 | ● |
| 29 | $(CH_3)_2CH$—*CH(Cl)—C(=O)—O—(Ph)—C(=N–N)–S—(Ph)—$C_{10}H_{21}$ | ● 128 | ● 147.5 | ● 148 | ● |

EXAMPLE 2

The inventive substances in Table 1 and the compounds listed in Tables 2 and 3 were used to fabricate the following mixtures:

Mixture 1
The mixture consists of:
No. 9 g (S)-5-n-nonyl-2-(4-(4-(2-chloro-3-methyl-butyryl-oxy)-benzoyloxy)-phenyl)-pyrimidine 40 mol-percent
No. 14 4-n-octyl-oxy-carbonyl-oxy-benzoic acid-(4-n-nonyl-phenylester) 60 mol-percent Mixture 2
The mixture consists of:
No. 14 4-n-octyl-oxy-carbonyl-oxy-benzoic acid-(4-n-nonyl-phenylester) 60 mol-percent
No. 11 (S)-4-n-octyl-oxy-benzoic acid-(4-(3-chloro-3-methyl-butyryl-oxy)-phenylester) 40 mol-percent Mixture 3
The mixture consists of:
No. 1 (S)-5-(4-n-hexyl-oxy-phenyl)-2-(4-(2-chloro-3-methyl-butyryl-oxy)-phenyl)-pyrimidine 40 mol-percent
No. 11 (S)-4-n-octyl-oxy-benzoic acid-(4-(3-chloro-3-methyl-butyryl-oxy)-phenylester) 60 mol-percent Mixture 4
The mixture consists of:
No. 11 (S)-4-n-octyl-oxy-benzoic acid-(4-(3-chloro-3-methyl-butyryl-oxy)-phenylester) 73 mol-percent
No. 13 (S)-4-n-Dodecyl-oxy-benzoic acid-(4-(2-chloro-3-methyl-butyryl-oxy)-phenylester) 13 mol-percent
No. 3 (SO-5-(4-n-decyl-phenyl)-2-(4-(2-chloro-3-methyl-butyryl-oxy)-pyrimidine 14 mol-percent Mixture 5
The mixture consists of:
No. 11 (S)-4-n-octyl-oxy-benzoic acid-(4-(3-chloro-3-methyl-butyryl-oxy)-phenylester) 46 mol-percent
No. 9 g (S)-5-n-nonyl-2-(4-(4-(2-chloro-3-methyl-butyryl-oxy)-benzoyl-oxy)-phenyl)-pyrimidine 15 mol-percent
No. 15 4-n-octyl-oxy-benzoic acid-(4-n-hexyl-oxy-phenylester) 16 mol-percent
No. 14 4-n-octyl-oxy-carbonyl-oxy-benzoic acid-(4-n-nonyl-phenylester) 23 mol-percent Mixture 6
The mixture consists of:
No. 11 (S)-4-n-octyl-oxy-benzoic acid-(4-(3-chloro-3-methyl-butyryl-oxy)-phenylester) 46 mol-percent
No. 3 (SO-5-(4-n-decyl-phenyl)-2-(4-(2-chloro-3-methyl-butyryl-oxy)-pyrimidine 15 mol-percent
No. 15 4-n-octyl-oxy-benzoic acid-(4-n-hexyl-oxy-phenylester) 16 mol-percent
No. 14 4-n-octyl-oxy-carbonyl-oxy-benzoic acid-(4-n-nonyl-phenylester) 23 mol-percent Mixture 7
The mixture consists of:
(S)-4-(2-chloro-3-methyl-butyryl-oxy)-4'-(4-n-octyl-oxy-benzoyl-oxy)-biphenyl 12 mol-percent
No. 10 (S)-4-(2-chloro-3-methyl-butyryl-oxy)-4'-(4-n-hexyl-oxy-benzoyl-oxy)-biphenyl 32 mol-percent
No. 9 g (S)-5-n-nonyl-2-(4-(4-(2-chloro-3-methyl-butyryl-oxy)-benzoyl-oxy)-phenyl)-pyrimidine 8 mol-percent
No. 16 5-n-nonyl-2-(4-n-octyl-oxy-phenyl)-pyrimidine 48 mol-percent Mixture 8
The mixture consists of:
(S)-4-(2-chloro-3-methyl-butyryl-oxy)-4'-(4-n-octyl-oxy-benzoyl-oxy)-biphenyl 18 mol-percent
No. 10 (S)-4-(2-chloro-3-methyl-butyryl-oxy)-4'-(4-n-hexyl-oxy-benzoyl-oxy)-biphenyl 49 mol-percent
No. 9 g (S)-5-n-nonyl-2-(4-(4-(2-chloro-3-methyl-butyryl-oxy)-benzoyl-oxy)-phenyl)-pyrimidine 13 mol-percent
No. 16 5-n-nonyl-2-(4-n-octyl-oxy-phenyl)-pyrimidine 20 mol-percent Mixture 9
The mixture consists of:
(S)-4-(2-chloro-3-methyl-butyryl-oxy)-4'-(4-n-octyl-oxy-benzoyl-oxy)-biphenyl 18 mol-percent
No. 10 (S)-4-(2-chloro-3-methyl-butyryl-oxy)-4'-(4-n-hexyl-oxy-benzoyloxy)-biphenyl 49 mol-percent
No. 9 g (S)-5-n-nonyl-2-(4-(4-(2-chloro-3-methyl-butyryl-oxy)-benzoyl-oxy)-phenyl)-pyrimidine 13 mol-percent
No. 17 2-(4-n-hexyl-oxy-phenyl)-5-n-nonyl-pyrimidine 20 mol-percent Mixture 10
The mixture consists of:
(S)-4-(2-chloro-3-methyl-butyryl-oxy)-4-(4-n-octyl-oxy-benzoyl-oxy)-biphenyl 12 mol-percent
No. 10 (S)-4-(2-chloro-3-methyl-butyryl-oxy)-4'-(4-n-hexyl-oxy-benzoyl-oxy)-biphenyl 32 mol-percent
No. 9 g (S)-5-n-nonyl-2-(4-(4-(2-chloro-3-methyl-butyryl-oxy)-benzoyl-oxy)-phenyl)-pyrimidine 8 mol-percent
No. 16 5-n-nonyl-2-(4-n-octyl-oxy-phenyl)-pyrimidine 20 mol-percent
No. 12 (S)-4-n-decyl-oxy-benzoic acid-(4-(2-chloro-3-methyl-butyryl-oxy)-phenylester) 28 mol-percent Mixture 11
The mixture consists of:
(S)-4-(2-chloro-3-methyl-butyryl-oxy)-4'-(4-n-octyl-oxy-benzoyl-oxy)-biphenyl 16 mol-percent
No. 10 (S)-4-(2-chloro-3-methyl-butyryl-oxy)-4'-(4-n-hexyl-oxy-benzoyl-oxy)-biphenyl 43 mol-percent
No. 9 g (S)-5-n-nonyl-2-(4-(4-(2-chloro-3-methyl-butyryl-oxy)-benzoyl-oxy)-phenyl)-pyrimidine 10 mol-percent
No. 17 2-(4-n-hexyl-oxy-phenyl)-5-n-nonyl-pyrimidine 20 mol-percent
No. 12 (S)-4-n-decyl-oxy-benzoic acid-(4-(2-chloro-3-methyl-butyryl-oxy)-phenylester) 11 mol-percent These mixtures have the following transition temperatures:

| Mixture | K | $S_c$ | $S_A$ | CH | I |
|---|---|---|---|---|---|
| 1 | 22.5 | 47 | — | 90 | |
| 2 | 34 | 37 | 56 | 110 | |
| 3 | 36 | 66 | — | 99 | |
| 4 | 33 | 35.5 | 75 | 77.5 | |
| 5 | 16 | 41 | 43 | 81.5 | |
| 6 | 18 | 35 | 76 | 86.5 | |
| 7 | 19 | 80 | 93 | 114 | |
| 8 | 44 | 100 | 108 | 135 | |
| 9 | 32 | 100.5 | 106 | 191 | |
| 10 | 30 | 66 | 95 | 113 | |
| 11 | 38 | 91.5 | 104 | 129 | |
| 12 | 32 | 80 | 103 | 127.5 | |

The following examples specify fabrication methods for the inventive compounds.

Example 3

Fabrication of (S)-2-(4-(2-chloro-3-methyl-butyryl-oxy)-phenyl)-5-(4-hexyl-oxy-phenyl)-pyrimidine (No. 1)

A. 2-(4-hydroxy-phenyl)-5-(4-hexyl-oxy-phenyl)-pyrimidine 0.01 mol 4-hydroxy-benzamidine-hydrochloride and 0.01 mol 3-dimethylamino-2-(4-hexyl-oxy-phenyl)-N,N-dimethylpropene-2-ammonium perchlorate are heated in 100 ml triethylamine for eight hours under reflux. After cooling, the mixture is poured over ice/conc. $H_2SO_4$ (200 g: 25 ml). The precipitate is suctioned off and is recrystallized several times from methanol. Yield: 2.6 g (75 percent of theoretical). M: 155° C.

B. (S)-2-(4-(2-chloro-3-methyl-butyryl-oxy)-phenyl)-5-(4-hexyl-oxy-phenyl)-pyrimidine 0.77 g/0.005 mol (s)-2-chloro-3-methyl-butyryl-chloride are added to a solution of 0.005 mol 2-(4-hydroxy-phenyl)-5-(4-hexyl-oxy-phenyl)-pyrimidine, 0.6 ml triethylamine and 50 ml absolute toluene. The acid chloride was produced according to a well-known method from the optically active α-amino acids.

The product is allowed to stand for one day at room temperature. It is then heated for one hour at 80 deg C. on a water bath. After filtering off the precipitate, the solvent is distilled off, and the residue is recrystallized several times from ethanol.

The yields are 60 to 70 percent of the theoretical yield.

The liquid crystalline melting behavior is specified in the tables.

EXAMPLE 4

A. Fabrication of (S)-(+)-3-hydroxy-butyric acid ethyl ester

A slurry is made with 200 g fresh baker's yeast in a solution of 300 g saccharose in 1.6 l fresh water at 30° C., and this slurry is gently agitated at 30° C. After an hour, under strong agitation, 0.15 moles distilled aceto-acetic ester are added, and the mixture is gently agitated for 24 hours at 25°–30° C. Subsequently, a solution of 200 g saccharose in 1 l water at 35 deg C. is added by portions. After strongly agitating for one hour, 0.15 moles acetoacetic ester are added once again. The mixture is agitated for 50 hours at 25°–30° C. Then it is suctioned over infusorial earth, and the residue is washed twice, each time with 100 ml water. The combined aqueous phases are saturated with NaCl and are extracted five times, each time with 500 ml ether. After separating and drying the organic phase over $Na_2SO_4$, it is concentrated by evaporation in a rotating evaporator down to 50–80 ml. Fractional distillation of the residue yields (S)-(+)-3-hydroxy-butyric acid ethyl ester in a yield amounting to 65–75 percent of theoretical.

| ee = 84% | $K_{p12}$ = 73° C. | $(\alpha)_D^{25}$ = +36.2° |
| | | $(CH_{Cl_3}; C = 1.3)$ |

B. Fabrication of (R)-(−)-3-chlorobutyric acid ethyl ester 0.24 moles (S)-(+)-3-hydroxy-butyric acid ethyl ester in 100 ml benzene are added to 0.07 moles anhydrous $ZnCl_2$ while agitating and while excluding moisture. Subsequently, 0.72 moles $SOCl_2$ are added, and the product is agitated at room temperature for two days. Then the reaction mixture is treated with saturated $NaHClO_3$ solution. After separating off the aqueous phase, it is dried with $Na_2SO_4$. The solvent is distilled off, and the residue is fractionally distilled. One obtains (R)-(−)-chlorobutyric acid ethyl ester with a yield of 65 percent.

| $K_{p16}$ = 68° C. | $(\alpha)_D^{25}$ = −14.36° |
| | $(CH_{Cl_3}; C = 4.7)$ |

C. Fabrication of (R)-(−)-3-chlorobutyrylchloride 0.07 moles (R)-(−)-3-chlorobutyric acid ethyl ester together with 100 ml concentrated hydrochloric acid are strongly agitated until there is a clear solution. Subsequently, the product is maintained at 37–40 deg C. for three days, while gently agitating. It is then diluted with 100 ml water, saturated with NaCl, and is extracted with ether three times, each time with 100 ml ether. The organic phase is dried with $Na_2SO_4$, and then the solvent is removed at the rotating evaporator. The residue is fractionally distilled in vacuum. The yield of (R)-(−)-3-chlorobutyrylchloride amounts to 70–75 percent of theoretical.

$K_{p30}$ = 125° C.

0.04 moles (R)-(−)-3-chlorobutyric acid are added to 0.06 moles $SOCl_2$, and are allowed to remain standing at room temperature for 24 hours while moisture is excluded. Then the temperature of the mixture is maintained at 42° C. for one and a half hours. Subsequently, it is fractionally distilled into an ice-cooled receiver.

Yield: 70–75 percent of theoretical

| $K_{p15}$ = 45° C. |
| $(\alpha)_D^{25}$ = −13.7° |
| $(CHCl_3; C = 7.34)$ |

D. Esterification of (R)-(−)-3-chlorobutyrylchloride with phenols and alcohols $1.7 \times 10^{-3}$ moles of the respective alcohol or phenol in 15–30 ml THF are placed in a 50 ml Erlenmeyer flask with a $CaCl_2$ tube. After the solution is cooled to −30° C., $2.13 \times 10^{-3}$ moles (R)-(−)-3-chlorobutyrylchloride and $1.7 \times 10^{-3}$ moles pyridine are added successively while the solution is being stirred. After agitating for 10 minutes at −30° C., the reaction mixture is allowed to stand for two days at −20 deg C. Then the mixture is placed into 300 ml ice-cold 5 percent hydrochloric acid. If the ester precipitates, it is suctioned off, and is recrystallized from methanol, hexane, or benzene.

If the ester does not crystallize out in the 5 percent hydrochloric acid, the mixture is extracted with ether three times, is dried over $Na_2SO_4$, and is subsequently distilled. The yield of the corresponding esters is 30 to 70 percent of theoretical.

We claim:

1. A chiral halogenated alkyl group containing ferroelectric liquid crystal compound of the formula

wherein $R^1$ is $C_lH_{2l+1}$—, $(CH_3)_2CH$—, $(CH_3)_2CH$—$CH_2$—, or $C_2H_5$—$CH(CH_3)$—, in which $l=3-12$,
$R^2$ is $C_kH_{2k+1}$— or $C_kH_{2k+1}O$—, in which $k=1-12$,
X is Cl or F,

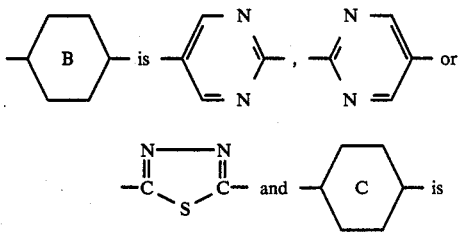

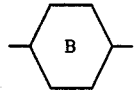

with the proviso that if is

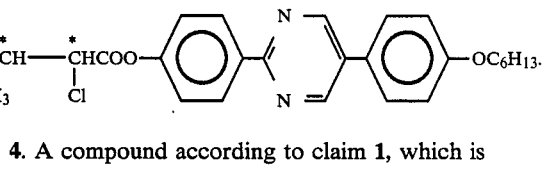

$R^1$ is only $C_2H_5$—$CH(CH_3)$—.

2. A compound according to claim 1, in which

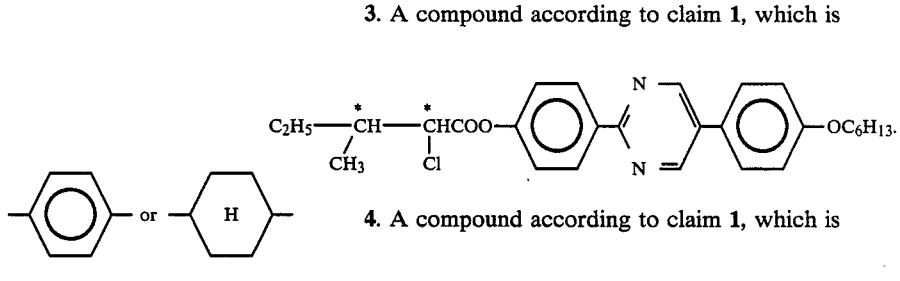

3. A compound according to claim 1, which is

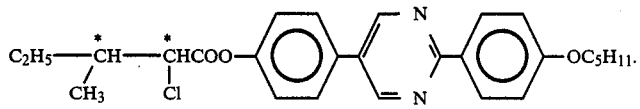

4. A compound according to claim 1, which is

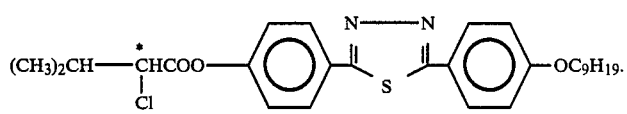

5. A compound according to claim 1, which is

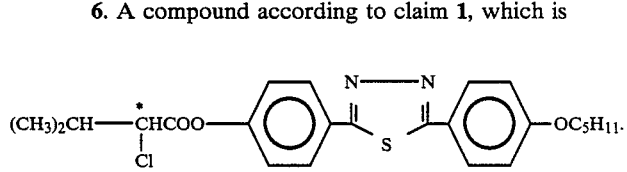

6. A compound according to claim 1, which is

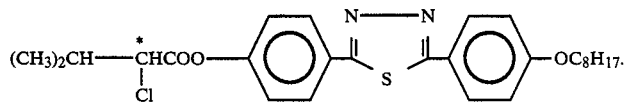

7. A compound according to claim 1, which is

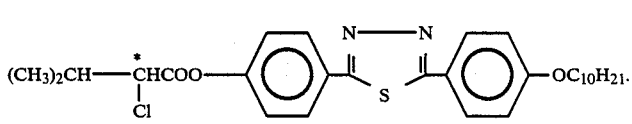

8. A compound according to claim 1, which is

9. A compound according to claim 1, in which

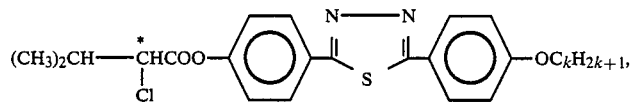

wherein k=1-12.

10. A fast switching display device with memory properties containing a compound according to claim 1.

11. A fast switching display device with memory properties containing a compound according to claim 2.

12. A fast switching display device with memory properties containing a compound according to claim 3.

13. A fast switching display device with memory properties containing a compound according to claim 4.

14. A fast switching display device with memory properties containing a compound according to claim 5.

15. A fast switching display device with memory properties containing a compound according to claim 6.

16. A fast switching display device with memory properties containing a compound according to claim 7.

17. A fast switching display device with memory properties containing a compound according to claim 8.

18. A fast switching display device with memory properties containing a compound according to claim 9.

* * * * *